United States Patent [19]
Roine et al.

[11] Patent Number: 5,949,193
[45] Date of Patent: Sep. 7, 1999

[54] PLASMA DEVICE WITH RESONATOR CIRCUIT PROVIDING SPARK DISCHARGE AND MAGNETIC FIELD

[75] Inventors: Johannes Roine, Ympäristötekniikka; Matti Asikainen, Maantiekylä, both of Finland

[73] Assignee: Valtion Teknillinen Tutkimuskeskus, Espoo, Finland

[21] Appl. No.: 09/051,451

[22] PCT Filed: Oct. 10, 1996

[86] PCT No.: PCT/FI96/00535

§ 371 Date: Aug. 14, 1998

§ 102(e) Date: Aug. 14, 1998

[87] PCT Pub. No.: WO97/14278

PCT Pub. Date: Apr. 17, 1997

[30] Foreign Application Priority Data

Nov. 10, 1995 [FI] Finland ..................................... 954843

[51] Int. Cl.⁶ ................................. H05H 1/30; H05H 1/32
[52] U.S. Cl. ................. 315/111.51; 356/316; 219/121.48
[58] Field of Search ........................... 315/111.21, 111.31, 315/111.41, 111.51; 219/121.48, 121.36; 356/316; 313/231.41, 231.51, 231.61; 250/426

[56] References Cited

U.S. PATENT DOCUMENTS

| 3,296,410 | 1/1967 | Hedger | 315/111.51 X |
| 3,541,625 | 11/1970 | Burggraaf | 373/24 |
| 4,638,489 | 1/1987 | Thornblom et al. | 373/22 |
| 4,766,351 | 8/1988 | Hull et al. | 315/111.51 X |

FOREIGN PATENT DOCUMENTS

| 371128 | 6/1990 | European Pat. Off. . |
| 602764 | 6/1994 | European Pat. Off. . |
| 673186 | 9/1995 | European Pat. Off. . |
| 673369 | 2/1990 | Switzerland . |
| 2271044 | 3/1994 | United Kingdom . |
| 91/01077 | 7/1990 | WIPO . |
| 93/12633 | 12/1992 | WIPO . |

OTHER PUBLICATIONS

Impedance Laser Spectroscopy in a Small RF–Excited Neon Discharge, Froake et al. Mikrochimica Acta, Springer–Vertag 113, pp. 349–355 (1994).

Optogalvanic Spectroscopy with rf Discharge, Optics Communication, vol. 38, No. 5,6, pp. 364–368, Sep. 1, 1981, Suzuki.

Characterization of Near–Infrared Atomic Emission from a Radio–Frequency Plasma for Selective Detection in Capillary Gas Chromatography, R. J. Skelton, Jr. et al., Applied Spectroscopy, vol. 44, No. 5, 1990, pp. 853–857.

*Primary Examiner*—Justin P. Bettendorf
*Attorney, Agent, or Firm*—Andrus, Sceales, Starke & Sawall

[57] ABSTRACT

The present invention relates to a procedure and a device for forming a plasma. The plasma generated can be used e.g. to examine the concentrations of elements contained e.g. in different gases, such as flue gases. The spark discharge and magnetic field used to form and maintain the plasma are produced by means of the same capacitor-coil resonator circuit. The device of the invention allows a very stable and controlled plasma to be achieved.

14 Claims, 7 Drawing Sheets

PLASMA DEVICE WITH RESONATOR CIRCUIT PROVIDING SPARK DISCHARGE AND MAGNETIC FIELD

BACKGROUND OF THE INVENTION

The present invention relates to a procedure and to a device for forming a plasma.

Elementary analyses of gas or aerosol samples are currently performed by subjecting a sample gas flow to a high temperature using external energy. Generally the sample gas is mixed with a gas that easily transforms into plasma, e.g. argon, helium or nitrogen, which may also be a component of the gas mixture under analysis. When the sample gas becomes sufficiently hot, the electrons in the in atoms of the elements become excited, and the wavelength of the light quantum or photon produced when the electrons are de-excited is characteristic of each element and its electron ring. By examining the light quanta, it is possible to determine the elements and their amounts contained in the sample.

As is known, the external energy can be produced using various systems. Previously known is an induction heater, which uses magnetic flux to transfer energy into the gas to be heated. A problem with the use of magnetic flux is how to "ignite" the gas, i.e. how to achieve a sufficient degree or ionization to induce the plasma state of the gas. A small gas quantity cannot receive a sufficient amount of energy from the magnetic flux, and this leads to the need for large apparatus using a high volume of gas flow. On the other hand, if small amounts of gas are used, the magnetic field has to be generated using a very high frequency, typically a frequency of several gigahertz. Conventionally, this problem is solved by using a spark between two electrodes to "ignite" the gas. The spark is created in the area where plasma is to be developed and it is extinguished after a plasma flame has been set up. This is not an automatic system, because if the plasma decays in consequence of an external disturbance, such as a power failure, gas supply failure or the like, it has to be ignited again with a spark.

Another prior-art method is to use only a high-voltage spark to produce a plasma. In this case, a gas is ionized using an electric spark until a breakdown occurs and the gas is converted into plasma. However, the spark is not extinguished after a plasma has been generated, but the spark is used to transfer the energy required by the plasma to the gas. As the required high power is transferred by means of a spark, the spark discharge is very unstable and difficult to control, causing serious; disturbances in the analysis of sample gases.

SUMMARY OF THE INVENTION

The object of the percent invention is to eliminate the drawbacks mentioned above.

A specific object of the present invention is to produce a procedure and a device for forming a plasma which allow a stable and controlled plasma to be generated with flue gas samplets for the purpose of determining the percentages of elements present in the flue gas samples.

Another object of the present invention is to produce a plasma forming device that works on a continuous principle, i.e. when the plasma reverts into gas, the device acts automatically so that the gas is again converted into plasma.

A further object of the present invention is to produce a procedure and a device which enable a plasma to be generated and maintained with a power demand significantly lower than in prior-art devices.

As for the features characteristic of the invention, reference is made to the claims.

In the procedure of the invention for forming a plasma, a magnetic field is set up in a plasma forming space, a spark discharge is produced in the plasma forming space and a gas flow is passed into the plasma forming space against the magnetic field. Preferably the gas flow is applied in a direction perpendicular to the magnetic field, permitting the most effective transfer of electric energy from the magnetic field to the gas. According to the invention, plasma is generated in the plasma forming; space by means of the spark discharge and maintained by means of the magnetic field and spark discharge, in practice, however, the situation is such that when the power of the magnetic field is sufficient, the spark has only a slight significance for the plasma. However, since the spark discharge exists continuously, the procedure of the invention is automatic, As compared with prior art, the present invention has the advantage that plasma is formed automatically both at the first "ignition" and during operation when the plasma has reverted back into gas due to a disturbance. Moreover, the arrangement of the invention allows a significant reduction in the energy consumption. This is because in the device of the invention the energy can be applied accurately to the plasma forming region and used for the generation of plasma. In addition, the circuit used in the device of the invention has a good efficiency.

Another advantage of the present invention as compared with prior art is that no high voltage or high power needs to be used in the amplifier which feeds the electric circuit producing the magnetic field and spark discharge.

A further advantage of the present invention as compared with prior art is that, in the device of the invention, no large quantities of gas or high frequencies need to be used.

In a preferred embodiment of the present invention, the magnetic field and the spark discharge are produced by means of substantially the same resonator circuit, consisting of a capacitor and a coil connected in series. The load of the circuit, connected in parallel with the coil, is the plasma forming space, which contains gas. As compared with the conventional parallel connection, the series connection has the advantage that, when the load impedance falls as the gas is converted into plasma, the amplifier feeding the resonator circuit sees an impedance—the impedance caused by the capacitor—independent of the load impedance.

The frequency of the resonator circuit—a series connection of a capacitor and a coil—is automatically so selected that the circuit works at the resonant frequency. In this case, the magnitudes of capacitance and reactance are equal, compensating each other. A suitable frequency is in the RF range, typically in the range of 100 kHz–3 MHz. When frequencies higher than this are used, it is possible to use the normal transmission path matching, i.e. a parallel connection of a coil and a capacitor, which is used in prior-art devices.

In a preferred case, the form and characteristics of the plasma being generated are controlled by adjusting the power of the magnetic field and spark discharge and regulating the flow of the gas used. Furthermore, it is preferable to keep the power of the spark discharge constant and under control so that the discharge will not cause any extra disturbance in the process of determining the presence of elements.

The device of the invention for forming a plasma comprises a power supply for supplying the power required for the formation of plasma, a plasma forming space, which is open in relation to its environment, an electric circuit, which is electrically connected to the power supply to produce a magnetic field and a spark discharge in the plasma forming space, and a gas channel communicating with the plasma forming space for passing a gas into the plasma forming space and out of it via its open part. According to the invention, the electric circuit comprises a resonator circuit consisting of a series connection of a coil and a capacitor and arranged to connect the electric power needed for forming a plasma to the plasma forming space.

As for the advantages of the device of the invention, reference in made to the advantages of the procedure of the invention.

In a preferred embodiment, the device comprises a first electrode, which is electrically connected to a first potential of the electric circuit, and a second electrode, which is placed at a distance from the first electrode and electrically connected to a second potential in the electric circuit, said first and second potentials being substantially different in magnitude. Further, the electrodes are so disposed that a spark discharge takes place in the plasma forming space with the selected values of the first and second potentials. In a preferred embodiment, one of the potentials is the earth potential of the amplifier feeding the electric circuit. The first and second electrodes are needed especially when treating gases that are difficult to convert into plasma. Such gases include e.g. nitrogen. On the other hand, when treating gases that are easier to convert into plasma, the second electrode is not necessarily needed at all. Such gases include e.g. argon. In this case, the second potential consists in the surrounding space, and the spark discharge shoots from the tip of the first electrode out into space, e.g. through a coil placed in the direction of the tip. Resonance preferably prevails between the coil and the capacitor, and the spark jet can be directed through a torque tube with a magnetic field on it.

In a preferred embodiment, the coil is disposed in the vicinity of the plasma forming space in such a way that the magnetic field generated by the coil is perpendicular to the direction of the gas flow. In this case, the coil may be so disposed that the plasma forming space is inside the coil structure. On the other hand, the magnetic field produced by the coil is also present outside the coil, so it is possible to dispose the plasma forming space outside the coil. In practice, however, the tact is that the magnetic flux density is greatest inside the cell. The coil preferably comprises a specified number of successive spiral discs with crossed windings. In such a solution, the winding is arranged in a spiral pattern on a round disc, starting near the center of the disc.

BRIEF DESCRIPTION OF THE SEVERAL VIEWS OF DRAWING

In the following, the invention is described by the aid of examples of its embodiments by referring to the attached drawing, in which FIG. 1 presents a diagram representing a device as provided by the invention;

FIG. 2 presents a diagram representing a spiral disc forming part of the coil of the device in FIG. 1;

FIG. 3a presents a conventional circuit for generating a magnetic field;

FIG. 3b presents the circuit used in the device of FIG. 1 for generating a magnetic field and a spark discharge;

FIGS. 4–7 present simulation results for the circuits in FIG. 3a and FIG. 3b; and FIG. 8 presents a diagram representing another device according to the invention, resembling the device in FIG. 1.

DETAILED DESCRIPTION OF THE INVENTION

Figure 1:
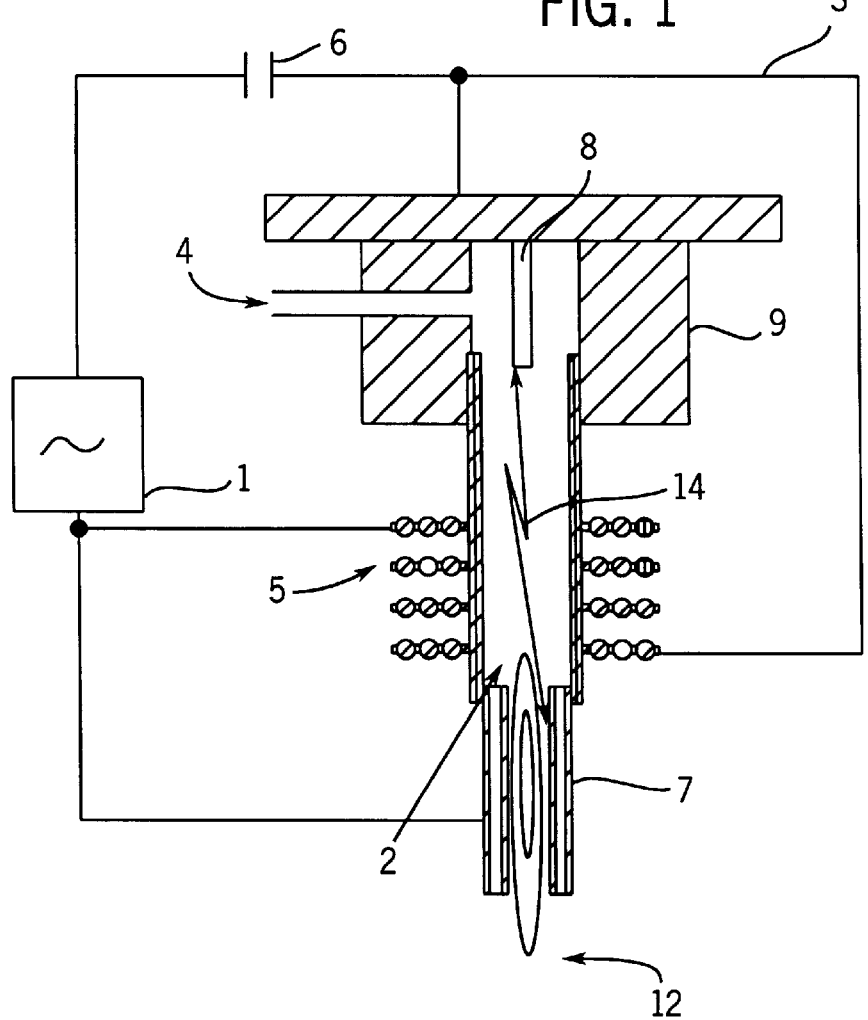

The device for generating a plasma as presented in FIG. 1 comprises a power supply 1, which preferably outputs a 200-V alternating voltage in the frequency range of 100 kHz–3 MHz, and a plasma forming space 2 open to its environment, into which space a gas to be ionized is supplied. Furthermore,, the device comprises an electric circuit 3, which according to the invention is a series connection of a coil and a capacitor and is electrically connected to the, power supply 1 to generate a magnetic field and a spark discharge 14 in the plasma forming space 2. As shown in FIG. 1, adjoined to the plasma forming space is a wall 7 which also functions as a first electrode, being electrically connected to the earth potential of the power supply 1. Further, the device comprises a gas channel 4 communicating with the plasma forming space 2 for passing gas into the plasma forming space and out of it via its open part. The device presented in FIG. 1 has a second bar-like electrode 8 attached to the frame and preferably made of an electrically conductive material. In FIG. 1, the plasma 12 being formed is represented by elliptic lines.

Figure 2:
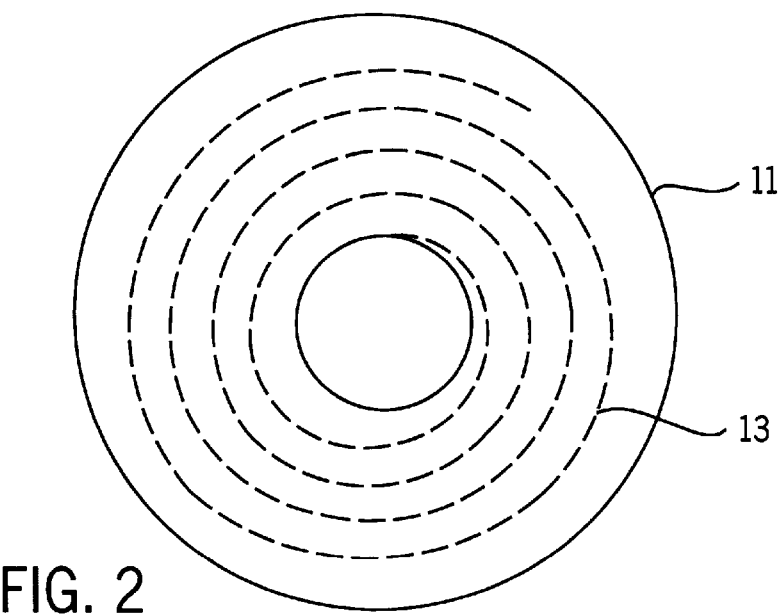

FIG. 2 presents a structure in which a conductor wire 13 is arranged in a spiral form on a disc-like body 11. The conductor wire 13 is wound alternately on either side of the disc 11. As the magnetic flux density in the circuit used in the device of the invention is proportional to the number of winding turns, the coil structure shown in FIG. 2 is very advantageous. Referring again to FIG. 1, the coil 5 comprises several spiral discs as shown in FIG. 2, connected in series. The cooling of such a coil structure is simple to implement and can be advantageously effected by blowing air into the gaps between the discs.

Figure 3A:
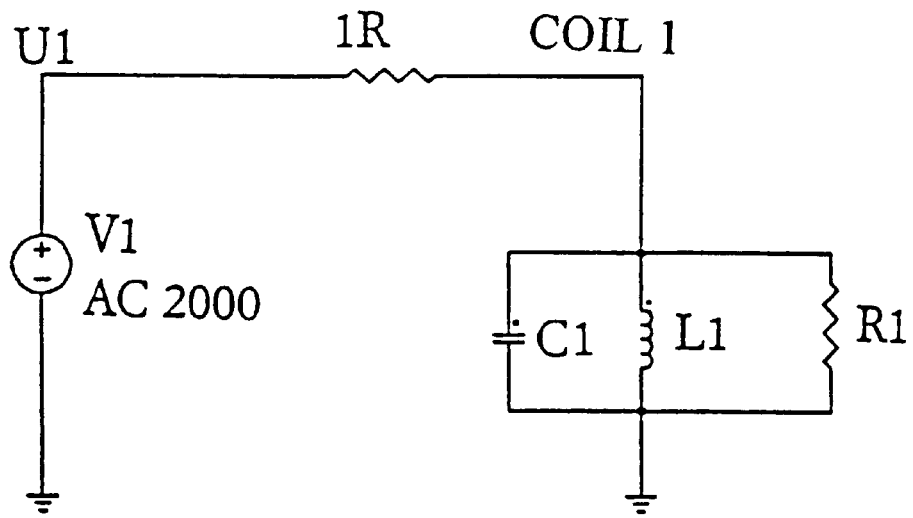
Figure 3B:
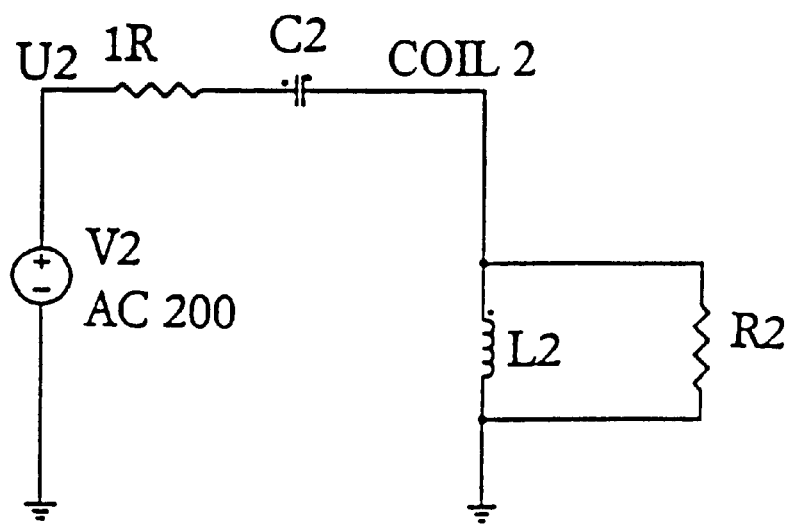
Figure 4:
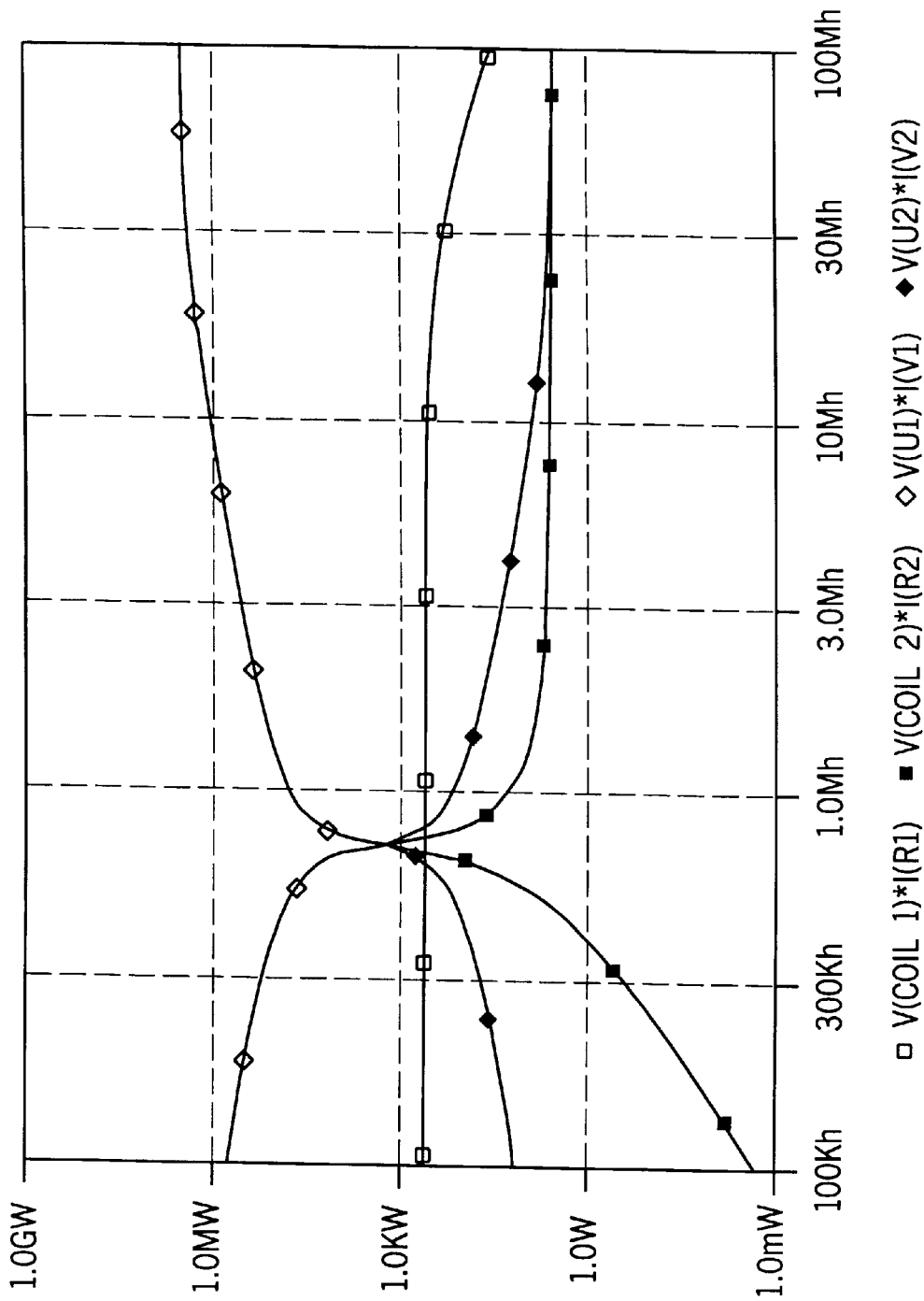
Figure 5:
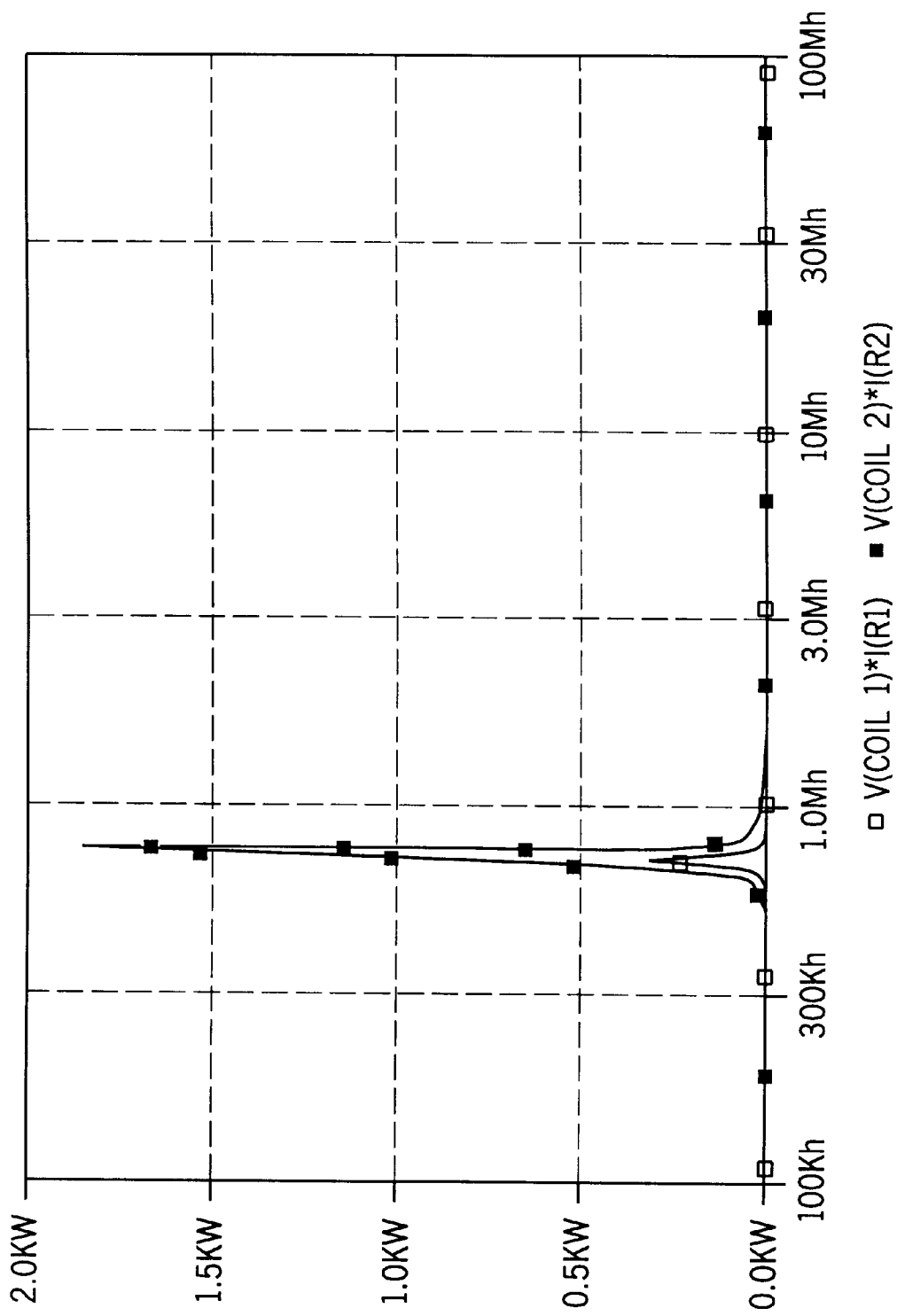

Referring to FIGS. 3a and 3b and to the curves shown in FIGS. 4–7, the series connection of the invention is compared with t:he conventional parallel connection used for matching the transfer path and generating a magnetic field. The action of the circuits was simulated using appropriate simulation software. The simulation results are presented in FIG. 4–7, in which the horizontal axis represents the frequency of the voltage supplied by the power supply 5 and also the frequency of the resonator. In FIG. 4 and 5, the vertical axis represents the power, in FIG. 6 the current and in FIG. 7 the voltage. In addition, the simulation program was given an external temperature value of 60° C.

The load impedance is represented in FIG. 3a and 3b by resistors R1 and R2, respectively. The load is connected in parallel with th,e coil producing the magnetic field, affecting the current that flows through the coil. When the gas is transformed into plasma, the electric conductivity of the gas is clearly improved, thus reducing the load impedance in this case, the high-power amplifier in FIG. 3a sees the fall in the load impedance directly and tries to supply more and more current into the load, so the circuit becomes unstable and difficult to control. In FIG. 3b, the load impedance of the amplifier does not change, because it has a constant value depending on capacitor C2. Therefore, the circuit remains stable and under control.

Figure 6:
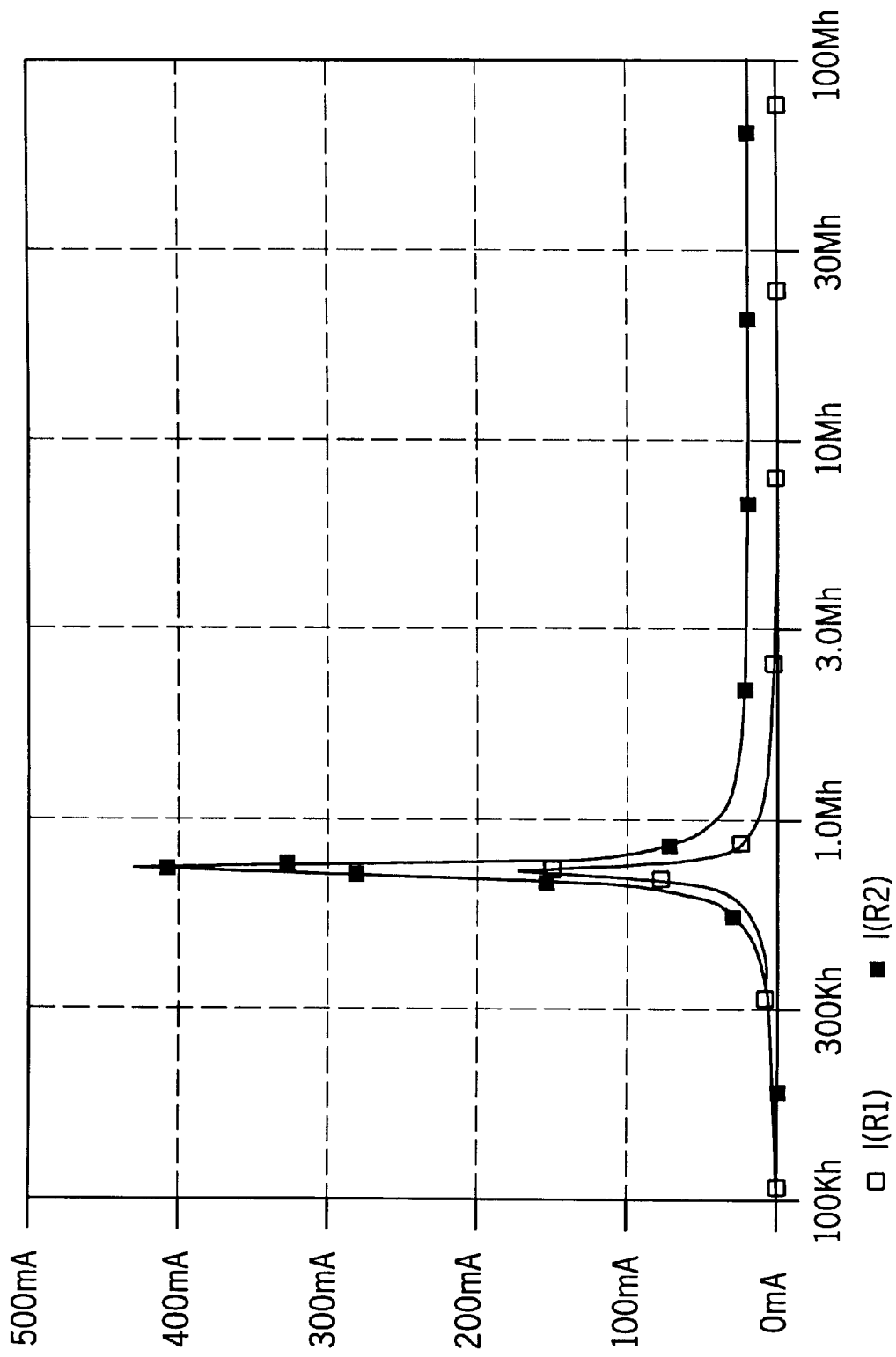

When the simulation results are examined, it can be seen from FIG. 4–7 that there is a definite difference between the conventional circuit and the circuit of the invention. FIG. 4 presents the power supplied by the amplifier into the resonator and the power fed into the coil as functions of frequency. As is clearly manifest from the figure, the highest power both from the amplifier and across the coil is achieved at the resonant frequency. FIG. 5 also graphically illustrates the difference between the conventional circuit and the circuit of the invention regarding the power transferred by the coil. FIG. 6 shows the current flowing through the load resistances R1 and R2 (plasma) as a function of frequency. From this, too, one can draw the conclusion that the resonator of the invention is more effective than the conventional resonator.

Figure 7:
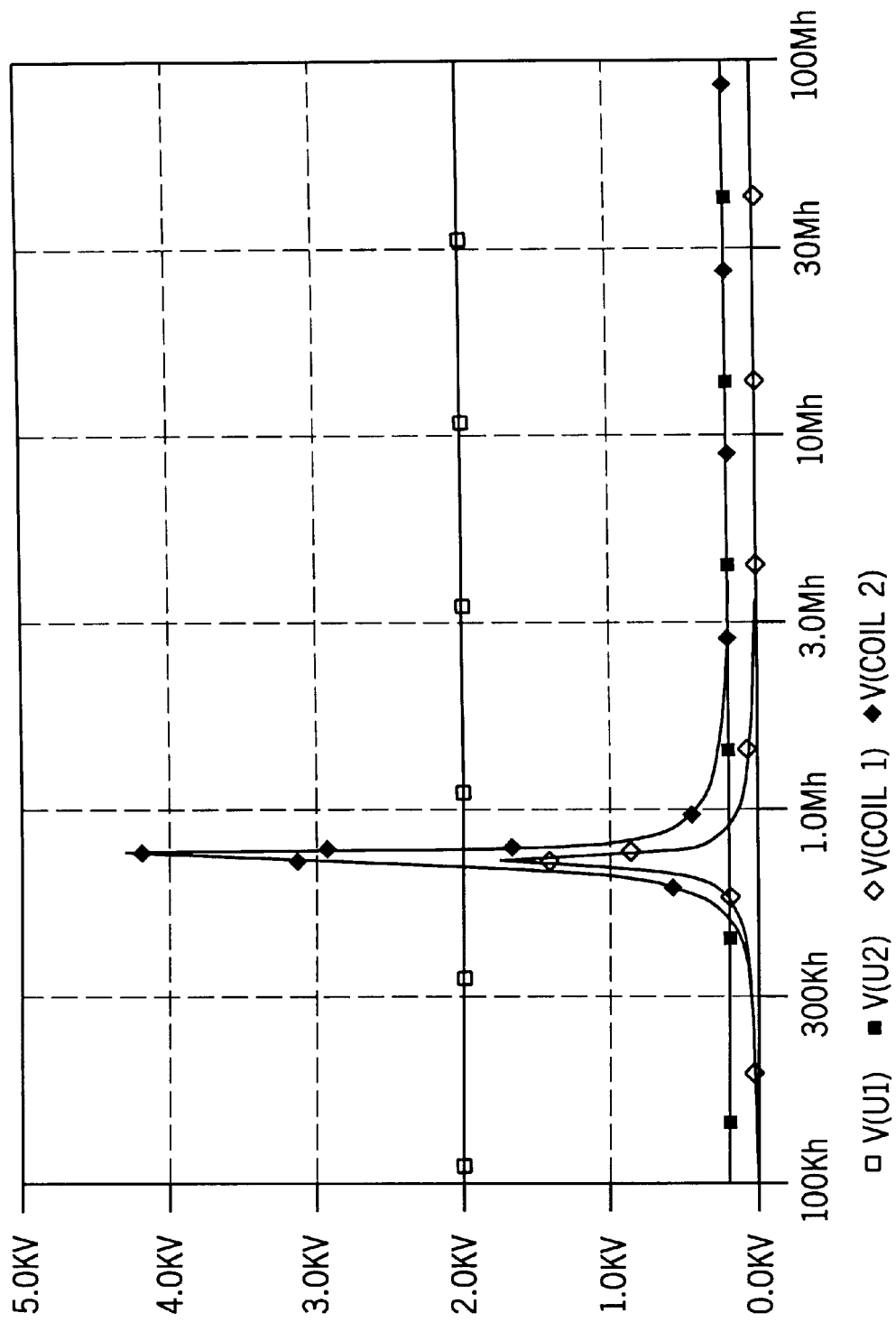

In FIG. 7, the voltage across the coil is presented as a function of frequent y and compared with the amplifier output voltage. It can be seen from FIG. 7 that the voltage across the coil, about 4 kV, achieved by the procedure of the invention is clearly higher than the amplifier output voltage (200 VAC). By contrast, the voltage across the coil achieved using the conventional parallel connection, about 1.8 kV, remains below the amplifier output voltage (2 kV).

Figure 8:
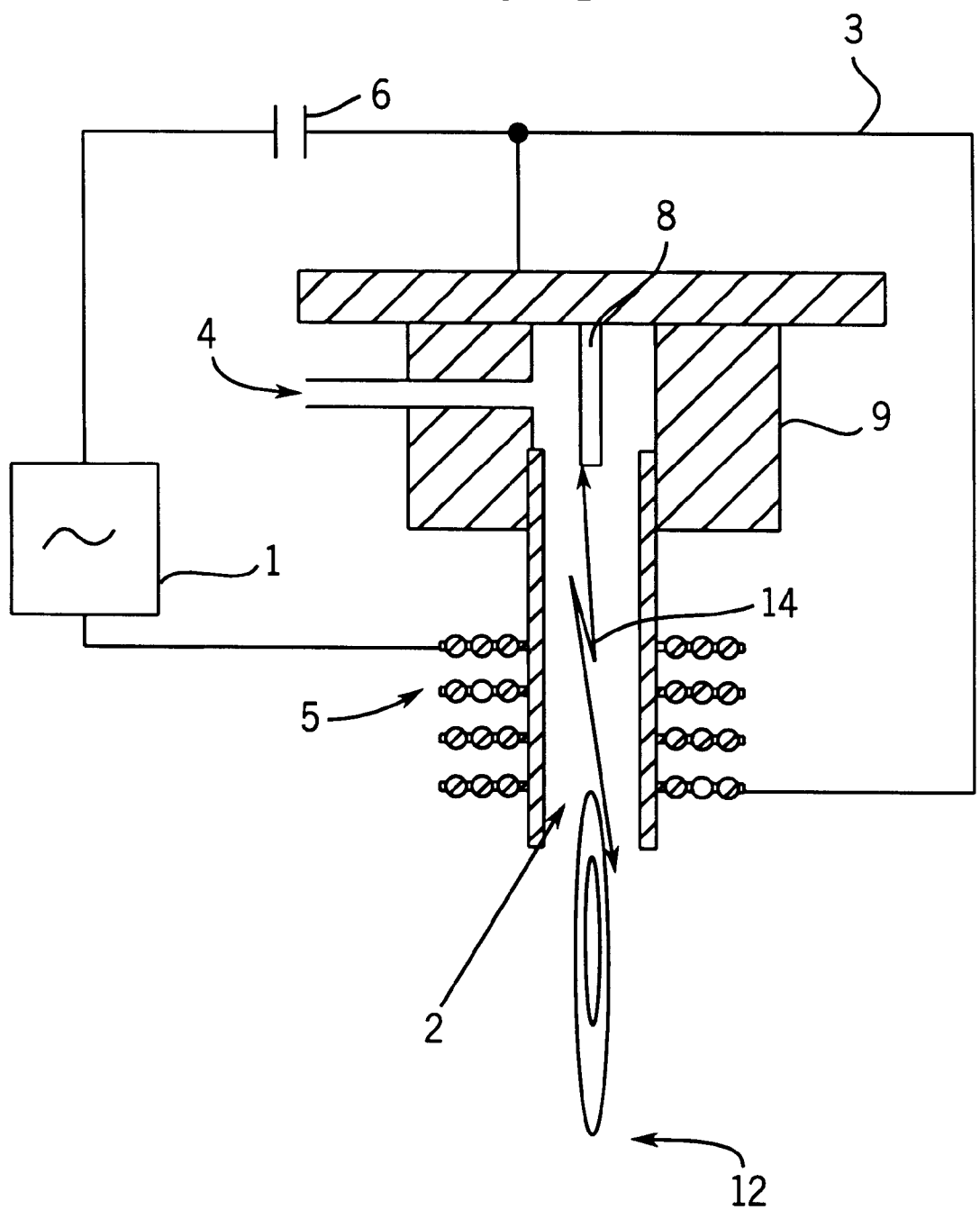

The device presented in FIG. 8 mainly corresponds to the device shown in FIG. 1. However, the device in FIG. 8 comprises only one electrode 8; the device has no separate electrode connected to the earth potential of the power supply 1. In the embodiment in FIG. 8, the plasma is formed in the plasma forming space 2 and shot into space through the torque tube formed by the coil 5, i.e. through the magnetic field generated by the coil. The device of FIG. 8 is particularly applicable in conjunction with treating gases convertible into the plasma state, such as argon.

As a summary, the following can be stated. Plasma generated by means of a spark and maintained by means of a spark and a magnetic field according to the invention becomes stabilized at the series resonance frequency because the net effect of the spark diminishes as the voltage rises and vice versa, and when the power transferred via the magnetic field to the plasma increases, the voltage falls and the effect of the magnetic field diminishes. Moreover, amplifier noise and other interference voltages in the series circuit are attenuated according to the proportion of the impedances.

The invention is not limited to the embodiment examples described above, but many variations are possible within the framework of the inventive idea defined by the claims.

We claim:

1. Procedure for forming a plasma, in which procedure a magnetic field is set up in a plasma forming space, a spark discharge is produced in the plasma forming space and a gas flow is passed into the magnetic field in the plasma forming space, wherein, the plasma is formed in the plasma forming space by means of the spark discharge and maintained by means of the magnetic field and spark discharge, and wherein the magnetic field and the spark discharge are produced by means of substantially the same resonator circuit, comprising a series connection of a capacitor and a coil.

2. Procedure as defined in claim 1, characterized in that the plasma is formed substantially within the coil.

3. Procedure as defined in claim 1, characterized in that the resonator circuit is supplied with an alternating electric current, the frequency of which is selected automatically so that the resonator circuit works at the resonant frequency.

4. Procedure as defined in claim 3, characterized in that the plasma is controlled by adjusting the power of the alternating current.

5. Procedure as defined in claim 1, characterized in that the plasma is controlled by adjusting the volume and/or rate of the gas flow.

6. Procedure as defined in claim 1, characterized in that the spark discharge is produced in the plasma forming space by means of an electrode placed in the gas flow and another electrode placed in conjunction with the plasma forming space.

7. Procedure as defined in claim 6, characterized in that the spark discharge is produced in the plasma forming space by means of the electrode placed in the gas flow by directing the spark discharge through the magnetic field generated by the coil into the surrounding space, which forms the other electrode.

8. Procedure as defined in claim 1, characterized in that the resonator circuit is supplied with an alternating electric current and that the plasma is controlled by adjusting the power of the alternating current.

9. Procedure as defined in claim 1, characterized in that the spark discharge is produced in the plasma forming space by means of an electrode placed in the gas flow by directing the spark discharge through the magnetic field generated by the coil into the surrounding space, which forms another electrode.

10. Device for forming a plasma, comprising
    a power supply (1) for supplying the power required for forming a plasma;
    a plasma forming space (2), which in open to the environment;
    an electric circuit (3), which is electrically connected to the power supply to produce a magnetic field and a spark discharge in the plasma forming space; and
    a gas channel (4) communicating with the plasma forming space for passing a gas into the plasma forming space and out of it via its open part, and wherein the electric circuit comprises a resonator circuit which comprises a series connection of a coil (5) and a capacitor (6) and arranged to connect the electric power required for forming a plasma to the plasma forming space (2) so that the magnetic field and the spark discharge are produced by means of substantially the said resonator circuit.

11. Device as defined in claims 10, characterized in that the plasma forming space is disposed inside the coil (5).

12. Device as defined in claim 10, characterized in that the coil comprises a specified number of spaced coaxial discs (11) with spiral windings.

13. Device as defined in claim 10, characterized in that the device comprises a first electrode (7), which is electrically connected to a first potential of the electric circuit, and a second electrode (8), which is placed at a distance from the first electrode and electrically connected to a second potential of the electric circuit, said first and second potentials being substantially different in magnitude; and that the electrodes are so disposed that a spark discharge takes place in the plasma forming space (2) with the selected values of the first and second potentials.

14. Device as defined in claim 10, characterized in that the coil (5) is disposed in the vicinity of the plasma forming space (2) in such a way that the magnetic field generated by the coil is perpendicular to the direction of the gas flow.

* * * * *